United States Patent [19]

Hokari et al.

[11] 4,348,260

[45] Sep. 7, 1982

[54] METHOD FOR INHIBITING POLYMERIZATION OF CONJUGATED DIENES

[75] Inventors: Hiroshi Hokari; Iwaki Nishitai, both of Kamakura, Japan

[73] Assignee: Nippon Zeon Co., Ltd., Tokyo, Japan

[21] Appl. No.: 210,334

[22] Filed: Nov. 25, 1980

[30] Foreign Application Priority Data

Dec. 6, 1979 [JP] Japan .............................. 54-157384

[51] Int. Cl.$^3$ .............................................. B01D 3/40
[52] U.S. Cl. ...................................... 203/9; 585/810; 585/833; 585/865
[58] Field of Search .................... 203/9; 585/809, 810, 585/833, 862, 865

[56] References Cited

U.S. PATENT DOCUMENTS 3,405,189 10/1968 Sakuragi et al. ......................... 203/9
3,436,438 4/1969 Takao et al. ............................. 203/9

*Primary Examiner*—Frank Sever
*Attorney, Agent, or Firm*—Sherman & Shalloway

[57] ABSTRACT

In a process for separating a conjugated diene from a hydrocarbon mixture containing the conjugated diene by extractive distillation using dimethyl formamide as an extractive solvent, a method for inhibiting polymerization of the conjugated diene in the dimethyl formamide at a high temperature which comprises using furfural and furfural polycondensates as polymerization inhibitors, and controlling the amounts of the polymerization inhibitors such that about 0.01 to about 2% by weight, based on the solvent, of furfural and about 0.5 to about 10% by weight, based on the solvent, of the furfural polycondensates are present in a total amount of about 1 to about 12% by weight, based on the solvent, throughout the entire separating process.

2 Claims, No Drawings

METHOD FOR INHIBITING POLYMERIZATION OF CONJUGATED DIENES

This invention relates to a method for inhibiting polymerization of conjugated dienes. More specifically, it relates to a method for inhibiting polymerization of butadiene, isoprene and 1,3-pentadiene in dimethyl formamide at a relatively high temperature.

An extractive distillation method or solvent absorption method using a polar solvent has been known as a technique for separating butadiene of high purity in a high yield from a hydrocarbon mixture containing butadiene, for example the so-called $C_4$ hydrocarbon fraction consisting mainly of n-butane, i-butane, n-butene, i-butene and butadiene, or for separating isoprene or 1,3-pentadiene of high purity in a high yield from a hydrocarbon mixture containing isoprene and 1,3-pentadiene, for example the so-called $C_5$ hydrocarbon fraction consisting mainly of n-pentane, i-pentane, n-pentene, isoamylene, 1,3-pentadiene, isoprene and cyclopentadiene. Dimethyl formamide, N-methyl pyrrolidone and acetonitrile, for example, are known as the solvent used in this method.

When such a method is operated, a solvent containing a conjugated diene such as butadiene, isoprene or 1,3-pentadiene is inevitably exposed to relatively high temperatures of, for example, 80° to 160° C. or higher. This results in polymerization of the conjugated diene in the solvent to form an insoluble polymer. Consequently, the precipitated polymer blocks the apparatus, and a film of the polymer is formed on the inner wall of the apparatus. Because of these drawbacks, it is practically impossible to perform the operation continuously over an extended period of time.

In particular, when dimethyl formamide is used as an extraction solvent, formation of a polymer occurs vigorously, and the continuous operation becomes more difficult. Dimethyl formamide, however, is chemically stable, and its boiling point is moderate. Hence, it is advantageous in view of solvent loss and heating. Moreover, dimethyl formamide has greater ability to adsorb butadiene, isoprene and 1,3-pentadiene than the other solvents, and is available at low price. Accordingly, if the formation of a polymer in dimethyl formamide can be inhibited, it can be an economically advantageous solvent.

Generally, at room temperature or temperatures below it, polymerization of conjugated dienes can be inhibited by the addition of well-known polymerization inhibitors such as hydroquinone, 4-t-butyl catechol, β-naphthylamine, methylene blue and sodium nitrite. But when the solvent is subjected to heat-treatment for a long period at a relatively high temperature of 80° to 160° C. or higher, the effect of the above-exemplified polymerization inhibitors is reduced drastically so that they cannot inhibit formation of polymers of conjugated dienes.

It is an object of this invention therefore to inhibit polymerization of a conjugated diene in dimethyl formamide at a relatively high temperature which is used as an extractive solvent, thereby making it possible to perform extractive distillation continuously for an extended period of time.

For this purpose, the addition of various polymerization inhibitors such as furfural, benzaldehyde, nitrobenzene and N-methyl pyrrolidone has already been proposed (for example, Japanese Patent Publications Nos. 20281/68 and 19881/70). These polymerization inhibitors fully exhibit their inhibiting effects on conjugated dienes, but when a solution of the conjugated diene is exposed to high temperatures, furfural, in particular, is abruptly degraded and loses its effect completely. If it is incessantly added according to the rate of its consumption, the degradation product builds up in the solution and reduces the extracting ability of the solvent.

The present inventors have made extensive investigations about the aforesaid problem, and found that when a solution obtained by adding furfural to a dimethyl formamide solvent containing a conjugated diene is treated at a high temperature, a polycondensate of furfural, a polycondensate of furfural and the conjugated diene, and a polycondensate of furfural and dimethylamine generated by the decomposition of dimethyl formamide are formed, and that although the mixture (to be referred to as a furfural polycondensates) of these polymers does not have a sufficient inhibiting effect on the polymerization of the conjugated diene, when it is present in a suitable proportion together with furfural in dimethyl formamide, this mixture can effectively inhibit polymerization of the conjugated diene.

Thus, the present invention provides, in a process for separating a conjugated diene from a hydrocarbon mixture containing the conjugated diene by extractive distillation using dimethyl formamide as an extractive solvent, a method for inhibiting polymerization of the conjugated diene in the dimethyl formamide at a high temperature which comprises using furfural and furfural polycondensates as polymerization inhibitors, and controlling the amounts of the polymerization inhibitors such that about 0.01 to about 2% by weight, based on the solvent, of furfural and about 0.5 to about 10% by weight, based on the solvent, of the furfural polycondensates are present in a total amount of about 1 to about 12% by weight, based on the solvent.

According to the method of this invention, polymerization of a conjugated diene such as butadiene, isoprene or 1,3-pentadiene can be effectively inhibited even in the presence of iron rust which is considered to promote polymerization of the conjugated diene. Accordingly, the separating operation can be operated stably over a long period of time without using an apparatus made of an expensive material such as stainless steel. The present invention also brings about the economical advantage that the amount of furfural required as a polymerization inhibitor can be greatly decreased.

The amounts of furfural and furfural polycondensates to be present in dimethyl formamide as polymerization inhibitors for conjugated dienes may vary over a wide range depending upon the operating conditions, the presence of iron rust, etc. The object of this invention can be achieved by controlling the amounts such that about 0.01 to about 2% by weight, especially about 0.05 to about 1% by weight, of furfural and about 0.5 to about 10% by weight, especially about 1 to about 6% by weight, of furfural polycondensates are present in a total amount of about 1 to about 12% by weight, especially about 1.1 to about 7% by weight. If the amount of furfural present is less than about 0.01% by weight, it has no polymerization inhibiting effect. If it is present in an amount of more than about 2% by weight, it only accelerates the formation of furfural polycondensates. On the other hand, when the amount of the furfural polycondensates is less than about 0.5% by weight, the consumption of furfural increases to cause economical disadvantage. If the amount exceeds about 10% by weight, they reduce the extracting ability of the solvent, and also become the cause of fouling.

The concentration of furfural in the dimethyl formamide solvent can be easily controlled by continuously or intermittently feeding a certain fixed amount of furfural into the solvent. On the other hand, the concentration of the furfural polycondensates in the solvent can be easily controlled by withdrawing a certain fixed amount of the solvent continuously or intermittently, separating the solvent from the furfural polycondensates, and recycling the polycondensates.

The furfural polycondensates may be those prepared in advance, or may be formed in situ. The essence of this invention is that the amounts of furfural and furfural polycondensates are controlled to the specified levels throughout the entire period of separating the conjugated diene by extractive distillation using dimethyl formamide as an extractive solvent.

The polymerization inhibiting effect in this invention can be increased by using in combination those substances which are well known as polymerization inhibitors or stabilizers for unsaturated compounds, for example sodium nitrite, methylene blue, phenolic compounds, and aromatic amines.

The method of this invention is effective even when a saturated hydrocarbon such as butane, n-pentane or i-pentane, an olefin such as n-butene, i-butene pentene-1, pentene-2 or 2-methylbutene-1, a higher acetylene such as methylacetylene or vinylacetylene, and cyclopentadiene are present in the extraction system. Accordingly, if the present invention is applied to the separation of butadiene from the $C_4$ fraction or separation of isoprene or 1,3-pentadiene from the $C_5$ hydrocarbon fraction by an extractive distillation method using dimethyl formamide, polymerization of butadiene, isoprene or 1,3-pentadiene can be almost completely inhibited, and no trouble of the apparatus owing to precipitated polymers is caused. The method of this invention can also be applied to the separation of paraffinic hydrocarbons and olefinic hydrocarbons from a hydrocarbon mixture containing small amounts of polymerizable conjugated diolefins and higher acetylenes.

The following Referential Example and Example illustrate the present invention specifically.

Referential Example

An autoclave was charged with equimolar amounts of dimethyl formamide, furfural and butadiene, and they were reacted at 160° C. for 24 hours while they were kept in contact with a large quantity of iron rust. After the reaction, the iron rust was removed, and the unreacted materials were distilled off to afford a mixture (i.e., the furfural polycondensates) consisting of a polycondensate of furfural, a polycondensate of furfural and butadiene and a polycondensate of furfural and dimethylamine in a ratio of 3:1:1. In the following Example, the furfural polycondensates were used.

EXAMPLE

A $C_4$ hydrocarbon mixture having the following composition was fed to a butadiene extractive distillation column at a rate of 10,000 kg per hour, and butadiene was continuously distilled extractively at a column bottom temperature of 120° C.

| | | |
|---|---|---|
| i-Butane | 0.8% | by weight |
| n-Butane | 9.5 | by weight |
| 1-Butene, i-butene | 38.7 | by weight |
| trans-2-Butene | 5.0 | by weight |
| cis-2-Butene | 4.0 | by weight |
| 1,3-Butadiene | 40.0 | by weight |
| 1,2-Butadiene Ethylacetylene Vinylacetylene Others | 2.0 | by weight |

The additives shown in the following table were added to dimethyl formamide as an extractive solvent, and the time which elapsed until a polymer of butadiene began to form in the solvent withdrawn from the bottom of the column by the extractive distillation was measured. The results are shown in the following table.

In Runs Nos. 5 to 12, the concentrations of furfural and the furfural polycondensates in the solvents were controlled so that they were the same as those of the initially fed inhibitors throughout the entire period of the extractive distillation.

| Run No. | Additives (wt. %) Furfural | Furfural polycondensates | Time elapsed until the formation of a butadiene polymer (hr) | Rate of consumption of furfural |
|---|---|---|---|---|
| 1 | 0.5 | — | 3 | Low |
| 2 | 1 | — | within 20 | High |
| 3 | 5 | — | within 50 | Very high |
| 4 | — | 5 | 5 | — |
| 5 | 1 | 0.1 | within 20 | High |
| 6 | 0.1 | 0.5 | 3 | Low |
| 7 (*) | 0.1 | 5 | above 100 | Very low |
| 8 (*) | 0.5 | 2 | above 100 | Very low |
| 9 (*) | 0.5 | 5 | above 300 | Very low |
| 10 (*) | 1 | 0.5 | above 100 | Low |
| 11 (*) | 1 | 3 | above 300 | Low |
| 12 | 5 | 3 | above 300 | Very high |

(*) Runs within the scope of the invention.

What we claim is:

1. In a process for separating a conjugated diene from a hydrocarbon mixture containing the conjugated diene by extractive distillation using dimethyl formamide as an extractive solvent in an amount sufficient to conduct said extractive distillation, a method for inhibiting polymerization of the conjugated diene in the dimethyl formamide at a sufficiently high temperature to otherwise cause polymerization of said conjugated diene, which comprises using furfural and furfural polycondensates as polymerization inhibitors, and controlling the amounts of the polymerization inhibitors such that about 0.01 to about 2% by weight, based on the solvent, of furfural and about 0.5 to about 10% by weight, based on the solvent, of the furfural polycondensates are present in a total amount of about 1 to about 12% by weight, based on the solvent, throughout the entire separating process.

2. The method of claim 1 wherein the amounts of the polymerization inhibitors are controlled such that about 0.05 to about 1% by weight, based on the solvent, of furfural and about 1 to about 6% by weight, based on the solvent, of the furfural polycondensates are present in a total amount of about 1.1 to about 7% by weight based on the solvent.

* * * * *